United States Patent
Matsuda et al.

(10) Patent No.: US 10,391,085 B2
(45) Date of Patent: Aug. 27, 2019

(54) METHODS OF TREATING GLIOBLASTOMA MULTIFORME USING IBUDILAST

(71) Applicant: MediciNova, Inc., La Jolla, CA (US)

(72) Inventors: Kazuko Matsuda, La Jolla, CA (US); Kerrie McDonald, Sydney (AU)

(73) Assignee: MediciNova, Inc., La Jolla, CA (US)

( * ) Notice: Subject to any disclaimer, the term of this patent is extended or adjusted under 35 U.S.C. 154(b) by 0 days.

(21) Appl. No.: 15/851,066

(22) Filed: Dec. 21, 2017

(65) Prior Publication Data

US 2018/0177772 A1 Jun. 28, 2018

Related U.S. Application Data

(60) Provisional application No. 62/438,170, filed on Dec. 22, 2016, provisional application No. 62/462,886, filed on Feb. 23, 2017.

(51) Int. Cl.
| | | |
|---|---|---|
| A61K 31/437 | (2006.01) | |
| A61K 45/06 | (2006.01) | |
| A61P 35/00 | (2006.01) | |
| A61K 31/4704 | (2006.01) | |
| A61K 31/495 | (2006.01) | |

(52) U.S. Cl.
CPC ........ *A61K 31/437* (2013.01); *A61K 31/4704* (2013.01); *A61K 31/495* (2013.01); *A61K 45/06* (2013.01); *A61P 35/00* (2018.01); *Y02A 50/465* (2018.01)

(58) Field of Classification Search
None
See application file for complete search history.

(56) References Cited

U.S. PATENT DOCUMENTS

| | | | |
|---|---|---|---|
| 6,395,747 B1 | 5/2002 | Sakoda et al. | |
| 8,138,201 B2 | 3/2012 | Kalafer et al. | |
| 9,114,136 B2 | 8/2015 | Kalafer et al. | |
| 9,314,452 B2 | 4/2016 | Kalafer et al. | |
| 2006/0160843 A1 | 7/2006 | Johnson et al. | |
| 2010/0260755 A1 | 10/2010 | Gammans et al. | |

OTHER PUBLICATIONS

McDonald, K. et al Cancer Res 2014, vol. 74, Sppl1 Annual Mtg of AACR, Abstr No. 2844.*
Chen et al., "The type Iv phosphodiesterase inhibitor rolipram induces expression of the cell cycle inhibitors p21(Cip1) and p27(Kip1), resulting in growth inhibition, increased differentiation, and subsequent apoptosis of malignant A-172 glioma cells," Cancer Biol. Ther., vol. 1, No. 3, pp. 268-276 (Jun. 2002).
Fujimoto et al., "Ibudilast, a phosphodiesterase inhibitor, ameliorates experimental autoimmune encephalomyelitis in Dark Aug. rats," J, Neuroimmunology, vol. 95, No. 1-2, pp. 35-42 (1999).
Gibson et al., "The Inhibitory Profile of Ibudilast Against the Human Phosphodiesterase Enzyme Family," European Journal of Pharmacology, vol. 538, pp. 39-42 (2006).
Jeffery et al., "The Preparation and Characterization of Poly(lactide-co-glycolide) Microparticles. II. The Entrapment of a Model Protein Using a (Water-in-Oil)-in-Water Emulsion Solvent Evaporation Technique", Pharmaceutical Research, vol. 10, No. 3, 1993, pp. 362-368.
Mizuno et al., "Neuroprotective role of phosphodiesterase inhibitor ibudilast on neuronal cell death induced by activated microglia," Neuropharmacology, vol. 46, pp. 404-411(2004).
Obernolte, R., et al. (1993) "The cDNA of a human lymphocyte cyclic-AMP phosphodiesterase (PDE IV) reveals a multigene family" Gene 129: 239-247.
Rile et al., "Potentiation of Ibudilast Inhibition of Platelet Aggregation in the Presence of Endothelial Cells," Thrombosis Research, 102 239-246 (2001).
Sanftner et al., "Cross-species comparisons of the pharmacokinetics of ibudilast," Xenobiotica, vol. 39, No. 12, pp. 964-977 (Nov. 2009). [Abstract].
Souness et al., "Possible Role of Cyclic AMP Phosphodiesterases in the Actions of Ibudilast on Eosinophil Thromboxane Generation and Airways Smooth Muscle Tone," British Journal of Pharmacology, 111:1081-1088 (1994).
Suzumura et al., "Ibudilast suppresses TNF.alpha. production by glial cells functioning mainly as type III phosphodiesterase inhibitor in NCS," Brain Research, 837:203-212 (1999).
Takuma et al., "Ibudilast attenuates actrocyte apoptsis via cyclic GMP signaling pathway in an in vitro reperfusion model," British Journal of Pharmacology, 133:841-848 (2001).
Wakimoto,et al., "Maintenace of primary tumor phenotype and genotype in glioblastoma stem cells," Neuro Oncol., vol. 14, No. 2, pp. 132-144 (Feb. 2012).
6th COGNO Conference Review, Oct. 25-26, 2013, 4 pages.
Wick, et al., "Efficacy and tolerability of Temozolomide in an Alternating Weekly regimen in Patients with Recurrent Glioma," J. Clin. Oncol., vol. 25, No. 22, pp. 3357-3361 (2007). [Abstract].
McDonald, et al., "Guided Therapeutic Strategy for Relapsed Glioblastoma Patients," Proceedings: AACR Annual Meeting Apr. 5-9, 2014. [Abstract].
International Search Report and Written Opinion issued in related International Patent Application No. PCT/US2017/067943, dated Feb. 22, 2018.

\* cited by examiner

*Primary Examiner* — Heidi Reese
(74) *Attorney, Agent, or Firm* — Foley & Lardner LLP

(57) ABSTRACT

Compositions and methods for treating glioblastoma or recurrent glioblastoma and its associated symptoms by administration of ibudilast (3-isobutyryl-2-isopropylpyrazolo[1,5-a]pyridine) or a pharmaceutically acceptable salt thereof.

16 Claims, 3 Drawing Sheets

| Phase | Screening | | Treatment phase | | | | | | | | | | Follow-up | Early Termination[f] |
|---|---|---|---|---|---|---|---|---|---|---|---|---|---|---|
| Visit Type | Day -XX to -8 | Day -7 | Day 1 Baseline | Month 1 | Month 3 | Month 4 | Month 6 | Month 7 | Month 9 | Month 10 | Month 12 | Month 12 1/2 End of Study | |
| | Clinic | Clinic | Clinic | Telephone | Clinic | Telephone | Clinic | Telephone | Clinic | Telephone | Clinic | Clinic | |
| Study Visit Number | 1 | 2 | 3 | 4 | 5 | 6 | 7 | 8 | 9 | 10 | 11 | 12 | ET |
| Informed consent | X[a] | X[b] | | | | | | | | | | | |
| Inclusion/exclusion criteria review | | X | X | | | | | | | | | | |
| Medical history | | X | | | | | | | | | | | |
| Medication history | | X | | | | | | | | | | | |
| Physical Examination | | X | | | X | | X | | X | | X | X | X |
| Body height | | X | | | | | | | | | | | |
| Body weight | | X | X | | X | | X | | X | | X | X | X |
| Vital signs (sitting) | | X | | | X | | X | X | X | X | X | X | X[d] |
| 12-lead ECG | | X | | | X | | X | | X | | X | | X[d] |
| CBC/CMP & CK | | X | | | X | | X | | X | | X | | X[d] |
| Serum pregnancy test | | X | | | | | | | | | | | |
| Urine pregnancy test | | | X | | X | | X | | X | | X | | X[d] |
| Plasma for PK & Biomarker | | | X | | | | | | X | | X | | X |
| Brain MRI | | | | | X | | X | | X | | X | X | X |
| Adverse event review | | | X | X | X | X | X | X | X | X | X | X | X |
| Concomitant med review | | | X | X | X | X | X | X | X | X | X | X | X |
| Study Drug Dispensing | | | X | | X | | X[c] | | X | | | | |
| Dispense/Review Patient Diary/Collect | | | X | | X | | X | | X | | X | X | X |
| Study Drug Accountability | | | | | X | | X | | X | | X | | X | a. A copy of the informed consent form (ICF) will be given to the patient for review.
b. Signing of the ICF will occur on Day -7.
c. Assessments to be done for early termination for any reason. Other assessments/procedures to be done at PI discretion, if necessary
d. Assessments do not need to be performed if prior assessments were within one month of this early termination visit.

FIG. 3

METHODS OF TREATING GLIOBLASTOMA MULTIFORME USING IBUDILAST

CROSS-REFERENCE TO RELATED APPLICATIONS

This application claims the benefit of and priority to U.S. Provisional Application No. 62/438,170, filed Dec. 22, 2016, and U.S. Provisional Application No. 62/462,886, filed Feb. 23, 2017, both of which are incorporated by reference herein in their entirety.

FIELD

The present disclosure relates generally to methods for treating glioblastoma multiforme (GBM), also known as glioblastoma, and/or recurrent glioblastoma (or recurrent GBM) comprising administering a therapeutically effective amount of ibudilast (3-isobutyryl-2-isopropylpyrazolo[1,5-a]pyridine).

BACKGROUND

The small molecule ibudilast (3-isobutyryl-2-isopropylpyrazolo[1,5-a]pyridine) is an inhibitor of macrophage inhibitory factor (MIF) (Cho et al PNAS-USA 2010 June 107: 11313-8) and selective inhibitor of cyclic nucleotide phosphodiesterases (PDEs) 3A, 4, 10A1 and 11A1 (Gibson et al., Eur J Pharmacol 538: 39-42, 2006). Ibudilast distributes well to the CNS (Smaller et al Xenobiotica 2009 39: 964-977) and at clinically-relevant plasma or CNS concentrations, ibudilast selectively inhibits macrophage migration inhibitory factor (MIF) and, secondarily. PDEs 3, 4, 10 and 11. Ibudilast also acts as a leukotriene D4 antagonist, an anti-inflammatory, a PAF antagonist, and a vasodilatory agent (Thompson Current Drug Reports). Ibudilast is thought to exert a neuroprotective role in the central nervous system of mammals, presumably via suppression of the activation of glial cells (Mizuno et al., Neuropharmacology 46: 404-411, 2004).

Ibudilast has been widely used in Japan for relieving symptoms associated with ischemic stroke or bronchial asthma. In recent clinical trials, its use in the treatment of multiple sclerosis (MS), an inflammatory disease of the central nervous system, has been explored (News. Medical-.Net; Pharmaceutical News, 2 Aug. 2005). As disclosed in this publication, this clinical trial was expected to treat "relapsing-remitting MS," however, no mention is made of progressive multiple sclerosis. In U.S. Pat. No. 6,395,747, ibudilast is disclosed as a treatment for multiple sclerosis, which is generally understood to mean relapsing and remitting multiple sclerosis, not progressive multiple sclerosis. U.S. Patent Application Publication No. 20060160843 discloses ibudilast for the treatment of intermittent and short term pain, however, this is not pain related to a progressive neurodegenerative disease. However, U.S. Pat. No. 9,314,452 discloses ibudilast as a treatment for amyotrophic lateral sclerosis, a progressive neurodegenerative disease. Similarly, U.S. Pat. No. 8,138,201 discloses ibudilast as a treatment for primary progressive multiple sclerosis and/or secondary progressive multiple sclerosis.

While the use of ibudilast for a number of varying indications has been reported to date, to the best of the Applicants' knowledge, its use in treating glioblastoma multiforme (GBM) or reaming forms thereof or refractory forms thereof has heretofore remained largely unexplored.

SUMMARY

In one aspect, provided herein is a method of treating a patient diagnosed with glioblastoma comprising administering to the patient a therapeutically effective amount of ibudilast or a pharmaceutically acceptable salt thereof.

In some embodiments, the ibudilast or pharmaceutically acceptable salt thereof is administered for at least 3 months. In some embodiments, the ibudilast or pharmaceutically acceptable salt thereof is administered for at least six months. In some embodiments, the ibudilast or pharmaceutically acceptable salt thereof is administered for at least one year. In some embodiments, the ibudilast or pharmaceutically acceptable salt thereof is administered for at least two years.

In some embodiments, the ibudilast or pharmaceutically acceptable salt thereof is administered at least once daily. In some embodiments, the ibudilast or pharmaceutically acceptable salt thereof is administered orally.

In some embodiments, the therapeutically effective amount of ibudilast or a pharmaceutically acceptable salt thereof is at least 30 mg/day. In some embodiments, the therapeutically effective amount of ibudilast or a pharmaceutically acceptable salt thereof is from 0.1 mg to 720 mg per day. In some embodiments, the therapeutically effective amount of ibudilast or a pharmaceutically acceptable salt thereof is from 30 mg to 200 mg per day. In some embodiments, the therapeutically effective amount of ibudilast of a pharmaceutically acceptable salt thereof is 30 mg to 720 mg daily. In some embodiments, the therapeutically effective amount of ibudilast or a pharmaceutically acceptable salt thereof is 60 mg to 600 mg daily. In some embodiments, the therapeutically effective amount of ibudilast or a pharmaceutically acceptable salt thereof is 100 mg to 480 mg daily.

In some embodiments, the therapeutically effective amount of ibudilast or a pharmaceutically acceptable salt thereof is selected from the group consisting of 30 mg/day, 60 mg/day, 90 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day 580 mg/day, 600 mg/day, 620 mg/day, 640 mg/day, 680 mg/day, and 720 mg/day.

In some embodiments, the therapeutically effective amount is administered as a single dose or is divided into two, three, or four doses.

In some embodiments, the ibudilast or a pharmaceutically acceptable salt thereof is administered as part of a combination therapy comprising at least one additional therapy. In some embodiments, the at least one additional therapy comprises one or more of radiation therapy, one or more other therapeutic agent, or electric field therapy.

In some embodiments, the one or more other therapeutic agent is approved and known to have a utility in cancer. In some embodiments, the one or more other therapeutic agent is temozolomide, carmustine, bevacizumab, procarbazine, hydroxyurea, irinotecan, lomustine, nimotuzumab, sirolimus, mipsagargin, cabozantinib, lomustine, onartuzumab, patupilone (Epothilone B), recombinant oncolytic poliovirus (PVS-RIPO), or any combination of one or more of the foregoing. In some embodiments, the one or more other therapeutic agent is temozolomide.

In some embodiments, the at least one additional therapy comprises laquinimod.

In some embodiments, the ibudilast or a pharmaceutically acceptable salt thereof and the at least one additional therapy are both administered continuously. In some embodiments, the ibudilast or a pharmaceutically acceptable salt thereof is administered continuously and the at least one additional therapy is administered periodically.

In one aspect, provided herein is a method of treating a patient suffering from recurrent glioblastoma comprising administering to the patient a therapeutically effective amount of ibudilast or a pharmaceutically acceptable salt thereof.

In some embodiments, the ibudilast or pharmaceutically acceptable salt thereof is administered for at least 3 months. In some embodiments, the ibudilast or pharmaceutically acceptable salt thereof is administered for at least six months. In some embodiments, the ibudilast or pharmaceutically acceptable salt thereof is administered for at least one year. In some embodiments, the ibudilast or pharmaceutically acceptable salt thereof is administered for at least two years.

In some embodiments, the ibudilast or pharmaceutically acceptable salt thereof is administered at least once daily. In some embodiments, the ibudilast or pharmaceutically acceptable salt thereof is administered orally.

In some embodiments, the therapeutically effective amount of ibudilast or a pharmaceutically acceptable salt thereof is at least 30 mg/day. In some embodiments, the therapeutically effective amount of ibudilast or a pharmaceutically acceptable salt thereof is from 0.1 mg to 720 mg per day. In some embodiments, the therapeutically effective amount of ibudilast or a pharmaceutically acceptable salt thereof is from 30 mg to 200 mg per day. In some embodiments, the therapeutically effective amount of ibudilast or a pharmaceutically acceptable salt thereof is 30 mg to 720 mg daily. In some embodiments, the therapeutically effective amount of ibudilast or a pharmaceutically acceptable salt thereof is 60 mg to 600 mg daily. In some embodiments, the therapeutically effective amount of ibudilast or a pharmaceutically acceptable salt thereof is 100 mg to 480 mg daily.

In some embodiments, the therapeutically effective amount of ibudilast or a pharmaceutically acceptable salt thereof is selected from the group consisting of 30 mg/day, 60 mg/day, 90 mg/day, 120 mg/day, 150 mg/day, 180 mg/day, 210 mg/day 240 mg/day, 270 mg/day, 300 mg/day, 360 mg/day, 400 mg/day, 440 mg/day, 480 mg/day, 520 mg/day, 580 mg/day, 600 mg/day 620 mg/day, 640 mg/day, 680 mg/day, and 720 mg/day.

In some embodiments, the therapeutically effective amount is administered as a single dose or is divided into two, three, or four doses.

In some embodiments, the ibudilast or a pharmaceutically acceptable salt thereof is administered as part of a combination therapy comprising at least one additional therapy. In some embodiments, the at least one additional therapy comprises one or more of radiation therapy, one or more other therapeutic agent, or electric field therapy.

In some embodiments, the one or more other therapeutic agent is approved and known to have a utility in cancer. In some embodiments, the one or more other therapeutic agent is temozolomide, carmustine, bevacizumab, procarbazine, hydroxyurea, irinotecan, lomustine, nimotuzumab, sirolimus, mipsagargin, cabozantinib, lomustine, onartuzumab, patupilone (Epothilone B), recombinant oncolytic poliovirus (PVS-RIPO), or any combination of one or more of the foregoing. In some embodiments, the one or more other therapeutic agent is temozolomide.

In some embodiments, the at least one additional therapy comprises laquinimod.

In some embodiments, the ibudilast or a pharmaceutically acceptable salt thereof and the at least one additional therapy are both administered continuously. In some embodiments, the ibudilast or a pharmaceutically acceptable salt thereof is administered continuously and the at least one additional therapy is administered periodically.

BRIEF DESCRIPTION OF THE FIGURES

FIG. 3 is a table showing the Schedule of Assessment for human studies.

DETAILED DESCRIPTION

Figure 1:
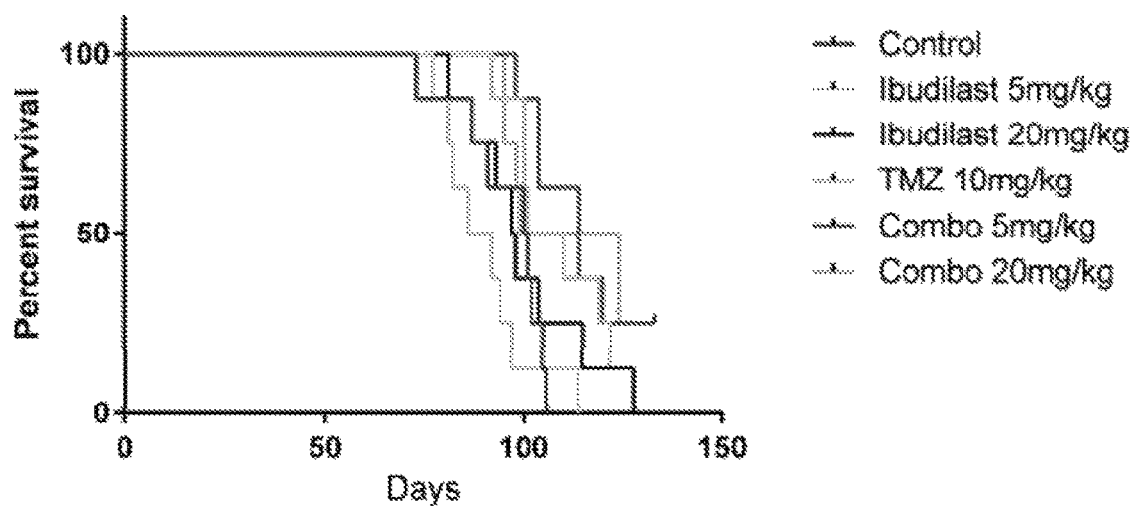
FIG. 1 is a graphical illustration of the percent survival of the mice treatment groups (ibudilast, temozolomide, or ibudilast and temozolomide) and the control group post-treatment.

The practice of the present disclosure will employ, unless otherwise indicated, conventional methods of chemistry, biochemistry, and pharmacology, within the skill of the art. Such techniques are explained fully in the literature. See, e.g.; A. L. Lehuinger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition): Remington: The Science and Practice of Pharmacy, A. Gentian), Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

All publications cited herein, including internet articles, the FDA Orange Book (available on the FDA's website), books, handbooks, journal articles, patents and patent applications, whether supra or infra, are hereby incorporated by reference in their entirety.

Definitions

Before describing the present disclosure in detail, it is to be understood that this disclosure is not limited to particular administration modes, patient populations, and the like, as such may vary, as will be apparent from the accompanying description and figures.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present disclosure, the following terminology will be used in accordance with the definitions described below.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

"Pharmaceutically acceptable excipient or carrier" refers to an excipient that may optionally be included in the compositions of the disclosure and that causes no significant adverse toxicological effects to the patient.

"Pharmaceutically acceptable salt" includes, but is not limited to, amino acid salts, salts prepared with inorganic acids, such as chloride, sulfate, phosphite, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, glucsptate and lactobionate salts. Similarly salts containing pharmaceutically acceptable cations include, but are not limited to, sodium, potassium, calcium aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent may include ibudilast or a pharmaceutically acceptable salt thereof.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

"Glial cells" refer to various cells of the central nervous system also known as microglia, astrocres and oligodendrocytes.

The terms "subject", "individual" or "patient" are used interchangeably herein and refer to a vertebrate, preferably a mammal. Mammals include, but are not limited to, mice, rodents, rats, simians, humans, farm animals, dogs, cats, sport animals and pets.

The terms "pharmacologically effective amount" or "therapeutically effective amount" of a composition or agent, as provided herein, refer to a nontoxic but sufficient amount of the composition or agent to provide the desired response, such as a reduction or reversal of progressive neurodegenerative diseases. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about," particularly in reference to a given quantity, is meant to encompass deviations of plus or minus five percent.

As used herein, the term "astrocyte" refers to a specific cell type

As used herein, the term "glioblastoma multiforme" or "glioblastoma" "or malignant glioma" are used interchangeably herein and refer to a brain tumor that arises from astrocytes.

As used herein, the term "treatment" or "treating" means any treatment of a disease or condition or associated disorder, in a patient, including:
  inhibiting the disease or condition, that is, arresting or suppressing the development of clinical symptoms, such as cachexia in cancer; and/or
  relieving the disease or condition that is, causing the regression of clinical symptoms, increasing overall survival or reducing tumor burden.

In some aspects, the term treating refers to an improvement in clinical outcomes. The term "clinical outcome" refers to any clinical observation or measurement relating to a patient's reaction to a therapy. Non-limiting examples of clinical outcomes include tumor response (TR), overall survival (OS), progression free survival (PFS), disease free survival, time to tumor recurrence (TTR), time to tumor progression (TTP), relative risk (RR), toxicity or side effect. "Overall Survival" (OS) intends a prolongation in life expectancy as compared to naïve or untreated individuals or patients. "Progression free survival" (PFS) or "Time to Tumor Progression" (TTP) indicates the length of time during and after treatment that the cancer does not grow. Progression-free survival includes the amount of time patients have experienced a complete response or a partial response, as well as the amount of time patients have experienced stable disease. "Tumor Recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer. "Time to Tumor Recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up. "Relative Risk" (RR), in statistics and mathematical epidemiology, refers to the risk of an event (or of developing a disease) relative to exposure. Relative risk is a ratio of the probability of the event occurring in the exposed group versus a non-exposed group.

"Treatment" or "treating" glioblastoma multiforme (GBM), also known as glioblastoma, or recurrent glioblastoma includes arresting the development or reversing the symptom or symptoms of glioblastoma and/or an improvement in clinical outcome of the patient suffering from glioblastoma or recurrent glioblastoma. Non-limiting example of improvements in clinical outcome include longer survival time, reduction in tumor size, non-growth in tumor size, and/or lack of exacerbation in neurological symptoms. Non-limiting examples of neurological symptoms include double vision, vomiting, loss of appetite, changes in mood and personality, changes in ability to think and learn, seizures, speech difficulty, and cognitive impairment.

Other objects, features and advantages of the present disclosure will become apparent from the following detailed description. It should be understood, however, that the detailed description and the specific examples, while indicating specific embodiments of the disclosure, are given by way of illustration only, since various changes and modifi-

Ibudilast

The methods of the disclosure for the treatment of glioblastoma or recurrent glioblastoma are based upon administration of the molecule, ibudilast. Ibudilast is a small molecule drug (molecular weight of 230.3) having the structure shown below.

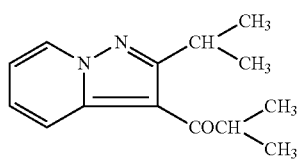

Ibudilast is also found under ChemBank ID 3227, CAS #50847-11-5, and Beilstein Handbook Reference No. 5-24-03-00396. Its molecular formula corresponds to $C_{14}H_{18}N_2O$. Ibudilast is also known by various chemical names including 2-methyl-1-(2-(1-methylethyl)pyrazolo(1,5-a)pyridin-3-yl)]-propanone; 3-isobutyryl-2-isopropylpyrazolo(1,5-a)pyridine]; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is Ketas®. Ibudilast, as referred to herein, is meant to include any and all pharmaceutically acceptable salt forms thereof, prodrug, forms (e.g., the corresponding ketal), solvates, and the like, as appropriate for use in its intended formulation for administration.

Ibudilast is an inhibitor of the macrophage inhibitory factor (MIF). Ibudilast is also a selective inhibitor of cyclic nucleotide phosphodiesterases (PDEs) 3A, 4, 10A1 and 11A1 (Gibson et al., Eur J Pharmacol 538: 39-42, 2006), and has also been reported to have leukotriene D4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals.

There are at least eight classes of PDEs: $Ca_2$+/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5): photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g., glial cells) resulting, in the suppression of both pro-inflammatory mediator and neuroactive mediator release. Ibudilast may also suppress the production of pro-inflammatory cytokines (IL-1β, TNF-α) and may enhance the production of the anti-inflammatory cytokines (IL-4, IL-10). References related to the foregoing include the following: Obernolte R., et al. (1993) "The cDNA of a human lymphocyte cyclic AMP phosphodiesterase (PDE IV) reveals a multigene family" Gene 129: 239-247; Rile, G., et al. (2001) "Potentiation of ibudilast inhibition of platelet aggregation in the presence of endothelial cells" Thromb. Res. 102: 239-246; Soulless, J. E., et al. (1994) "Possible role of cyclic AMP phosphodiesterases in the actions of ibudilast on eosinophil thromboxane generation and airways smooth muscle tone" Br. J. Pharmacol. 111: 1081-1088; Suzumura, A., et al. (1999) "Ibudilast suppresses TNF.alpha. production by glial cells functioning, mainly as type III phosphodiesterase inhibitor in CNS" Brain Res. 837: 203-212; Takuma, K., et al. (2001) "Ibudilast attenuates astrocyte apoptosis via cyclic GMP signaling pathway in an in vitro reperfusion model" Br. J. Pharmacol. 133: 841-848.

The use of rolipram (a PDE4 inhibitor) for treating glioblastoma has been suggested. See Chen et al., Cancer Biol. Ther. 2002, 1(3): 268-276. While rolipram showed positive results in cell assay studies and animal model studies, rolipram is not a great candidate for glioblastoma treatment in humans because of its poor penetration into the central nervous system (CNS). Ibudilast, on the other hand, exhibits good CNS penetration. (Sanftner et al Xenobiotica 2009 39: 964-977)

As stated previously, a reference to any one or more of the herein-described drugs, in particular ibudilast is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Methods of Administration

As set forth above, the present disclosure is directed to a method of treating a patient, including a human patient, diagnosed with glioblastoma or suffering from recurrent glioblastoma comprising administering to the patient a therapeutically effective amount of ibudilast or a pharmaceutically acceptable salt thereof. Such administering is effective to decrease the amount of glioblastoma or recurrent glioblastoma experienced by the patient, i.e., to result in a significant attenuation or even reversal of glioblastoma or recurrent glioblastoma, demonstrated in the accompanying Examples. Ibudilast or a pharmaceutically acceptable salt thereof is preferably administered at a daily dosage amount ranging from about 0.1 mg to 720 mg daily, from about 30 mg to 720 mg daily, from about 60 mg to 600 mg daily, or from about 100 mg to 480 mg daily.

The method of the disclosure may, in certain instances, comprise a step of selecting a patient experiencing glioblastoma or recurrent glioblastoma prior to administering ibudilast thereto.

Ibudilast or a pharmaceutically acceptable salt thereof may also be administered as part of a combination therapy comprising at least one additional therapy. In some embodiments, the at least one additional therapy comprises one or more of radiation therapy, one or more other therapeutic agent, or electric field therapy.

In some embodiments, the ibudilast or a pharmaceutically acceptable salt thereof and the at least one additional therapy are both administered continuously. In some embodiments, the ibudilast or a pharmaceutically acceptable salt thereof is administered continuously and the at least one additional therapy is administered periodically.

In some embodiments, the one or more other therapeutic agents is approved and known to have a utility in cancer. In some embodiments, the one or more other therapeutic agents comprises a phosphodiesterase-3 inhibitor. In some embodiments, the one or more other therapeutic agents comprises a phosphodiesterase-4 inhibitor. In some embodiments, the one or more other therapeutic agents comprises a macrophage inhibitory factor inhibitor. In some embodiments, the one or more other therapeutic agents comprises laquinimod. In a preferred embodiment, the one or more other therapeutic agents possesses a mechanism of action different from ibudilast.

Non-limiting examples of the one or more other therapeutic agents include temozolomide, carmustine, bevacizumab, procarbazine, hydroxyurea, irinotecan, lomustine, nimotuzumab, sirolimus, mipsagargin, cabozantinib, lomustine, onartuzumab, patupilone (Epothilone B), recombinant oncolytic poliovirus (PVS-RIPO), or ally combination of one or more of the foregoing.

Preferred methods of delivery of ibudilast-based therapeutic formulations for the treatment of glioblastoma or recurrent glioblastoma include systemic and localized delivery. Such routes of administration include but are not limited to, oral, intra-arterial, intrathecal, intraspinal, intranmuscular, intraperitoneal, intranasal, and inhalation routes.

More particularly, an ibudilast-based formulation of the present disclosure may be administered for therapy by any suitable route, including without limitation, oral, rectal, nasal, topical (including transdermal, aerosol, buccal and sublingual), vaginal, parenteral (including subcutaneous, intravenous, intramuscular, and intradermal), intrathecal, and pulmonary. In some embodiments, the ibudilast-based formulation is administered orally. In some embodiments, the ibudilast-based formulation is administered through an injection. The preferred route will, of course, vary with the condition and age of the recipient, the particular syndrome being treated, and the specific combination of drugs employed.

In some embodiments, the ibudilast or pharmaceutically acceptable salt thereof is administered orally. In some embodiments, the ibudilast or pharmaceutically acceptable salt thereof is administered through an injection.

An ibudilast composition of the disclosure, when comprising more than one active agent, may be administered as a single combination composition comprising a combination of ibudilast and at least one additional active agent effective in the treatment of glioblastoma or recurrent glioblastoma. In terms of patient compliance and ease of administration, such an approach is preferred, since patients are often adverse to taking multiple pills or dosage forms, often multiple times daily, over the duration of treatment. Alternatively, albeit less preferably, the combination of the disclosure is administered as separate dosage forms. In instances in which the drugs comprising the therapeutic composition of the disclosure are administered as separate dosage forms and co-administration is required, ibudilast and each of the additional active agents may be administered simultaneously, sequentially in any order, or separately.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the an, and will be adjusted to the requirements of each particular case. Generally, a therapeutically effective amount of ibudilast or pharmaceutically acceptable salt thereof will range from a total daily dosage of about. 0.1 mg/day to 720 mg/day, about 60-600 mg/day, or about 100-480 mg/day, or more preferably, in an amount between about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, the therapeutically effective amount of ibudilast or pharmaceutically acceptable salt thereof is from about 30-200 mg/day, administered as either a single dosage or as multiple dosages. In some embodiments, multiple dosages include two, three, or four doses per day.

Preferred dosage amounts include dosages greater than about 20 mg BID or TID. That is to say, a preferred dosage amount is greater than about 30 mg/day, 60 mg/day, 90 mg/day, 120 mg/day, 150 mg/day, 180 mg/day, 210 mg/day, 240 mg/day, 270 mg/day, 300 mg/day 360 mg/day, 400 mg/day, 440 mg/day, 480 mg/day, 520 mg/day, 580 mg/day, 600 mg/day, 620 mg/day, 640 mg/day 680 mg/day, and 720 mg/day or more.

In some embodiments, the therapeutically effective amount of ibudilast or pharmaceutically acceptable salt thereof is at least 30 mg/day, at least 40 mg/day, at least 50 mg/day, at least 60 mg/day, at least 70 mg/day, at least $0 mg/day, at least 90 mg/day at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, or at least 720 mg/day. In some embodiments, the therapeutically effective amount of ibudilast or pharmaceutically acceptable salt thereof is at least 60 mg/day. In some embodiments, the therapeutically effective amount of ibudilast or pharmaceutically acceptable salt thereof is at least 100 mg/day.

Depending upon the dosage amount and precise condition to be treated, administration can be one, two, three, or four times daily for a time course of one day to several days, weeks, months, and even years, and may even be for the life of the patient. Illustrative dosing regimes will last a period of at least about a week, from about 1-4 weeks, from 1-3 months, from 1-6 months, from 1-52 weeks, from 1-24 months, or longer. In some embodiments, the ibudilast or the pharmaceutically acceptable salt thereof is administered for three months or less. In some embodiments, the ibudilast or the pharmaceutically acceptable salt thereof is administered for at least three months. In some embodiments, the ibudilast or the pharmaceutically acceptable salt thereof is administered for at least six months. In some embodiments, the ibudilast or the pharmaceutically acceptable salt thereof is administered for at least one year. In some embodiments, the ibudilast or the pharmaceutically acceptable salt thereof is administered for at least two years. In some embodiments, the ibudilast or the pharmaceutically acceptable salt thereof is administered for at least three years.

In some embodiments, the therapeutically effective amount of ibudilast or the pharmaceutically acceptable salt thereof is administered in a single dosage per day. In some embodiments, the therapeutically effective amount of ibudilast or the pharmaceutically acceptable salt thereof is administered in two dosages per day. In some embodiments, the therapeutically effective amount of ibudilast or the pharmaceutically acceptable salt thereof is administered in three dosages per day. In some embodiments, the therapeutically effective amount of ibudilast or the pharmaceutically acceptable salt thereof is administered in four dosages per day.

In some embodiments, the ibudilast or pharmaceutically acceptable salt thereof is administered at least once daily. In some embodiments, the ibudilast or pharmaceutically acceptable salt thereof is administered at least twice daily.

Practically speaking, a unit dose of any given composition of the disclosure or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Treatment of Glioblastoma or Recurrent Glioblastoma

As noted above, in one aspect, the disclosure provides methods for treating a patient disposed with glioblastoma or suffering from recurrent glioblastoma comprising administering to the subject a therapeutically effective amount of ibudilast or a pharmaceutically acceptable salt thereof.

In some embodiments, the patient is a human patient.

Animal Models

The ability of ibudilast to treat glioblastoma or recurrent glioblastoma can be evaluated by any of the standard glioblastoma models known in the art. Examples of such models are described in Animal Models of Neurological Disease: Neurodegenerative Diseases. (Neuromethods) by Alan A. Boulton, Glen B. Baker, and Roger F. Butterworth (1992); Handbook of Laboratory Animal Science, Second Edition: Volumes I-III (Handbook of Laboratory Animal Science) by Jann Hau (Editor), Jr., Gerald L. Van Hoosier (Editor), (2004); Animal Models of Movement Disorders by Mark LeDoux (Editor), (2005); and Animal Models. of Cognitive Impairment (Frontiers in Neuroscience) (2006) by Edward D. Levin (Editor). Jerry J. Buccafrusco (Editor).

Formulations

In addition to comprising ibudilast or a pharmaceutically acceptable salt thereof, a therapeutic formulation of the disclosure may optionally contain one or more additional components as described below.

Excipients/Carriers

In addition to ibudilast or a pharmaceutically acceptable salt thereof, the compositions of the disclosure for treating glioblastoma or recurrent glioblastoma may further comprise one or more pharmaceutically acceptable excipients or carriers. Exemplary excipients include, without limitation, polyethylene glycol (PEG), hydrogenated castor oil (HCO), cremophors, carbohydrates, starches e.g., corn starch), inorganic salts, antimicrobial agents, antioxidants, binders/fillets, surfactants, lubricants (e.g., calcium or magnesium stearate), glidants such as talc, disintegrants, diluents, buffers, acids, bases, film coats, combinations thereof and the like.

A composition of the disclosure may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the disclosure are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A composition of the disclosure may also contain one or more antioxidants. Antioxidants are used to prevent oxidation, thereby preventing the deterioration of the drug(s) or other components of the preparation. Suitable antioxidants for use in the present disclosure include, for example, ascorbyl palmitate, butylated hydroxyanisole, butylated hydroxytoluene hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the disclosure may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient. In general, the amount of excipient present in an ibudilast composition of the disclosure is selected from the following: at least about 2%, 5%, 10%, 15%, 20%, 25%, 30%, 35%, 40%, 45%, 50%, 55%, 60%, 65%, 70%. 75%, 80%, 85%, 90%, or even 95% by weight.

These foregoing pharmaceutical excipients along with other excipients are described in "Remington: The Science & Practice of Pharmacy", 19th ed., Williams &. Williams, (1995), the "Physician's Desk Reference", 52.sup.nd ed., Medical Economics, Montvale, N.J. (1998), and Kibbe, A. H., Handbook of Pharmaceutical Excipients, 3.sup.rd Edition, American Pharmaceutical Association, Washington, D.C., 2000.

Other Actives

A formulation (or kit) in accordance with the disclosure may contain, in addition to ibudilast or a pharmaceutically acceptable salt thereof, one or more other therapeutic active agents effective in treating glioblastoma or recurrent glioblastoma. In some embodiments, the one or more other therapeutic agents comprises a phosphodiesterase-3 inhibitor. In some embodiments, the one or more other therapeutic agents comprises a phosphodiesterase-4 inhibitor. In some embodiments, the one or more other therapeutic agents comprises a macrophage inhibitory factor inhibitor. In some embodiments, the one or more other therapeutic agents comprises laquinimod. In a preferred embodiment, the one or more other therapeutic agents possesses a mechanism of action different from ibudilast.

Preferably, the one or more other therapeutic agent is one that possesses a mechanism of action different from that of ibudilast. Such active ingredients can be found listed in the FDA's Orange Book, Goodman & Gilman The Pharmacological Basis of Therapeutics, J. Griffith. Hardman, L. L. Limbird, A. Gilman, 11th Ed., 2005, The Merck Manual, 18th edition. 2007, and The Merck Manual of Medical Information 2003.

The dosage amounts provided above are meant to be merely guidelines the precise amount of a secondary active agent to be administered during combination therapy with ibudilast or the pharmaceutically acceptable salt thereof will, of course, be adjusted accordingly and will depend upon factors such as intended patient population, the particular progressive neuropathic disease symptom or condition to be treated, potential synergies between the active agents administered, and the like, and will readily be determined by one skilled in the art based upon the guidance provided herein.

Sustained Delivery Formulations

Preferably, the compositions are formulated in order to improve stability and extend the half-life of ibudilast or the pharmaceutically acceptable salt thereof. For example, ibudilast or the pharmaceutically acceptable salt thereof may be delivered in a controlled or extended-release formulation. Controlled or extended-release formulations are prepared by incorporating ibudilast or the pharmaceutically acceptable salt thereof into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, ibudilast or the pharmaceutically acceptable salt thereof can be encapsulated, adsorbed to, or associated with, particulate carriers. Examples of particulate carriers include those derived from poly-methyl methacrylate polymers, as well as microparticles derived from poly(lactides) and poly(lactide-co-glycolides), known as PLG. See, e.g., Jeffery et al., Pharm. Res. (1993) 10:362-368; and McGee et al., J. Microencap. (1996).

Extended release polymers suitable for this purpose are blown in the art and include hydrophobic polymers such as cellulose ethers. Non-limiting examples of suitable cellulose ethers include ethyl cellulose, cellulose acetate and the like; polyvinyl esters such as polyvinyl acetate, polyacrylic acid esters, methacrylic and acrylate polymers (pH-independent types); high molecular weight polyvinyl alcohols and waxes such as fatty acids and glycerides, methacrylic acid ester neutral polymers, polyvinyl alcohol-maleic anhydride copolymers and the like; ethylacrylate-methylmethacrylate copolymers; aminoalkyl methacrylate copolymers; and mixtures thereof.

Delivery Forms

The ibudilast or pharmaceutically acceptable salt thereof compositions described herein encompass all types of formulations, and in particular, those that are suited for systemic or intrathecal administration. Oral dosage forms include tablets, lozenges, capsules, syrups, oral suspensions, emulsions, granules, and pellets. In some embodiments, the oral dosage form is a tablet. In some embodiments, the tablet is an extended release tablet. In some embodiments, the oral dosage form is a capsule. In some embodiments, the capsule is an extended release capsule.

Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, an ibudilast or pharmaceutically acceptable salt thereof composition of the disclosure is one suited for oral administration.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known maimer. While this phase may comprise merely an emulsifier (otherwise known as an emulgent) it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx® (Aradigm), the Ultravente (Mallinkrodt), and the Aconi II® (Marquest Medical Products). A composition of the disclosure may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the disclosure are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the disclosure may also be an extended release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the disclosure may optionally include other agents conventional in the pharmaceutical arts and particular type of formulation being employed, for example, for oral administration forms, the composition for oral administration may also include additional agents as sweeteners, thickeners or flavoring agents.

Kits

Also provided herein is a kit containing at least one combination composition of the disclosure, accompanied by instructions for use.

For example, in instances in which each of the drugs themselves are administered as individual or separate dosage forms, the kit comprises ibudilast in addition to each of the thugs making up the composition of the disclosure, along with instructions for use. The drug components may be packaged in any manner suitable for administration, so long as the packaging, when considered along with the instructions for administration, clearly indicates the maimer in which each of the drug components is to be administered.

For example, for an illustrative kit comprising ibudilast and gabapentin, the kit may be organized by any appropriate time period, such as by day. As an example, for Day 1, a representative kit may comprise unit dosages of each of ibudilast and gabapentin. If each of the drugs is to be administered twice daily, then the kit may contain, corresponding to Day 1, two rows of unit dosage forms of each of ibudilast and gabapentin, along with in for the timing of administration. Alternatively, if one or more of the drugs differs in the timing or quantity of unit dosage form to be administered in comparison to the other drug members of the combination, then such would be reflected in the packaging and instructions. Various embodiments according to the above may be readily envisioned, and would of course depend upon the particular combination of drugs, in addition to ibudilast, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister paks, dessicants, and the like.

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

All references mentioned in this application, including any patents, published patent applications, books, handbooks, journal publications, or the FDA Orange Book are hereby incorporated by reference herein, in their entirety.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

EXAMPLES

Example 1

Ibudilast and Temozolomide Efficacy in Balb/c Nude Mice Harboring Patient Derived Glioblastoma Patient-derived cell line RN1 (2 μL) was intra-cranially injected into balb/c nude mice. The RN1 cell line was chosen because it is O(6)-methylguanine-DNA methyltransferase (MGMT) unmethylated and typically resistant to treatment with TMZ.

Once the balb/c nude mice arrived, they were allowed to acclimate to their new environment and the study participants for a period of 10 days. Mice were housed in groups of 4, and unless undergoing a procedure, were given free access to food and water at all times, Individual mice were identified via a unique ear punch number. A standard numbering system was used in which a specific ear punch location was associated with its own number.

Tumor Implantation 6-8 week old balb/c nude mice were used. All procedures, except autopsies, were carried out within a laminar flow cabinet. Tumors were induced following the procedure disclosed in Wakimoto H. et al. (2012) Neuro Oncol. 14(2): 132-44.Balb/c nude mice were weighed and held in groups of four. The mice received an analgesic 2 hours prior to primary human tumor cell implantation the mice were injected subcutaneously with 5 mg/kg Rimadyl (Carprofen). The animals were anesthetized via continuous mask inhalation of isoflurane (2.5-3%, 1 min oxygen for induction and 1-2.5%, 0.2 L/min oxygen for maintenance). The depth of anesthesia was assessed by toe pinch reflex (leg withdrawal) before the procedure began (cf. monitoring sheet #1), Using a number 11 scalpel blade, the skin on the head was cut sagittally (approximately from the level of the ears to the front of the eyes). This incision was large enough to allow identification of skull landmarks and prevent retracted skin from getting in the way of drilling. Using a stereotactic frame (small animal stereotactic frame, David KOPF Instruments, Germany), the head was clamped firmly in position by placing the side clamps on the bone approximately between the eyes and ears. These clamps not only functioned to keep the head from moving during the procedure (due to normal breathing) but also to kept the retracted skin in place so the skull remained accessible.

A 2 mm drill hole was made at the stereotactically in the right caudate putamen using the coordinates 1 mm anterior, 1.5 mm lateral, and 3.0 mm below the bregma. A micro-injector unit (holding a 2 μl Hamilton syringe with a 25 gauge needle) connected to the manipulating arm of the stereotactic device was used to inject a 2 μL solution containing 200,000 primary human tumor cells dorsoventrally (DV) at −3 from the skull surface, to deposit cells into the lateral portion of the striatum (right basal ganglia). All injections were made over a period of 10 minutes to ensure optimal parenchymal compliance. The micro-injector needle was retracted and the burr hole in the skull closed using bone-wax (Johnson & Johnson) in order to prevent extracranial tumor growth. Skin was closed using a tissue adhesive (Vetbond). Mice received sterile eye drops (Systane) throughout the procedure to avoid eye dryness.

The total duration of the implantation procedure was approximately 35 minutes. The whole procedure was performed above a thermostatically controlled warming pad to prevent a drop in animal temperature during surgery.

Post-surgical animals were moved to the recovery area, placed on bedding within an animal box, warmed using a small animal infrared heat lamp, and were monitored until they woke up, at which time they were returned to their housing (cf. monitoring sheet #1). Heat lamps were used instead of thermostatic controlled warming pads, as these pads were not able to sufficiently warm the mice through the floor of the animal box, which was used to keep the mice in a sterile environment while they recover from surgery. To prevent the mice from overheating, the temperature inside the box was monitored using a standard thermometer.

Treatment

Ibudilast

Two dosages of ibudilast were administered to the balb/c nude mince: 5 mg/kg and 20 mg/kg (both in 100 uL total volume). The dosage of ibudilast was extrapolated from multiple animal studies on rats looking at the treatment of multiple sclerosis (MS) disease and models of central neuropathic pain (Ellis et al. 2014; Reagan-shaw et al. 2008). Ibudilast showed no toxicity and was administered via gavage.

Temozolomide 10 mg/kg of temozolomide (TMZ) was administered to the balb/c nude mice through intraperitoneal injection.

RN1 (MGMT Unmethylated GBM)-Injected Balb/c Nude Mice

Five treatment groups were used as follows:
1. Ibudilast 5 mg/kg by gavage (n=8
2. Ibudilast: 20 mg/kg by gavage (n=8)
3. Combination 1: Ibudilast (5 mg/kg)+TMZ (10 mg/k) (n=8)
4. Combination Ibudilast (20 mg/kg)+TMZ (10 mg/kg) (n=8)
5. Control saline containing polyoxyethylene hydrogenated castor oil 60; 100 μL) (n=8)

For all of the treatment groups (except the control group), ibudilast was administered by gavage (daily) for approximately 59 days (until the last control mouse died) and TMZ was administered via intraperitoneal injection (daily) for two weeks.

Each treatment group contained eight animals. Approximately two animals from each control group were humanely euthanized at Day 40, Day 45. Day 50, and Day 60 in order to monitor tumor growth. This was because magnetic resonance imaging (MRI) is not sensitive enough to detect the tumor in vivo and there are no other means to detect the presence of the tumor other than humanely euthanizing the mice, removing the brain, fixing in paraffin and then sectioning the brain and staining with haeniotoxylin and eosin (H&E) upon confirmation that the tumor was present, the treatments were immediately started.

Tissue was collected from all animals at end points and biomarker analysis was conducted.

At approximately 43 days after tumor implantation, mice were treated with temozolomide (10 mg/kg) and/or ibudilast (5 mg/kg or 20 mg/kg). Ibudilast was administered in a solution of saline containing polyoxyethylene hydrogenated castor oil 60 using the gavage method (100 µl total volume) (Fujimoto et al., 1999 J Neuroimniunology 95:1-2, 35-42). Temozolomide was delivered by intraperitoneal injection (I.P.) in 0.1% dimethyl sulfoxide (DMSO, 180 µl total volume).

Monitoring

The body weight of each animal was measured twice a week in addition to routine daily monitoring by animal house staff (cf. monitoring sheet 42).

The animals started to lose 5-10% of their body weight the week before the appearance of neurological decline. At this particular time, animals were carefully monitored (twice daily) as neurological decline can occur rapidly. Typical signs of neurological decline include a hunched posture with an arched back, continuous circling, walking on tip-toes, balance issues, closed eyes, hyperactivity, and seizures. Neurological decline was scored (cf. monitoring sheet 43) for each animal.

Euthanasia

When signs of pain, distress or neurological decline were noted, animals were immediately euthanized by inhalation of a progressive overdose of carbon dioxide (cf. B.7). Animals were also immediately euthanized if they lost more than 20% of their body weight. If these signs were not observed, mice were euthanized by a progressive overdose of carbon dioxide no later than 260 days (37 weeks) following tumor induction.

When animals were euthanized, their brains were harvested and tumors were processed for immunohistochemical examination, molecular typing and preparation of cell stocks. Kaplan-Meier analysis was used to estimate survival from tumor induction.

Results

In all groups, the treatment of ibudilast alone or ibudilast in combination with temozolomide was well tolerated. The median survival of the untreated mice was 100.5 days. The medial survival time of the ibudilast 5 mg/kg and TMZ combination group was 114 days. The median survival time of the ibudilast 20 mg/kg and TMZ, combination group was 111.5 days. Additionally, one mouse in the ibudilast 5 mg/kg group and two mice in the ibudilast 20 mg/kg group survived longer than the longest surviving mouse in the control group.

All the mice in the control group died within 105 days (0% survival rate). At 105 days, the ibudilast 5 mg/kg group exhibited a 12% survival rate (one out of eight mice); the ibudilast. 20 mg/kg group exhibited a 25% survival rate (two out of eight mice); the ibudilast 5 mg/kg and TMZ combination group exhibited a 65.5% survival rate (five out of eight mice); and the ibudilast 20 mg/kg and TMZ combination group exhibited a 50% survival rate (four out of eight mice) (see FIG. 1).

Figure 2:
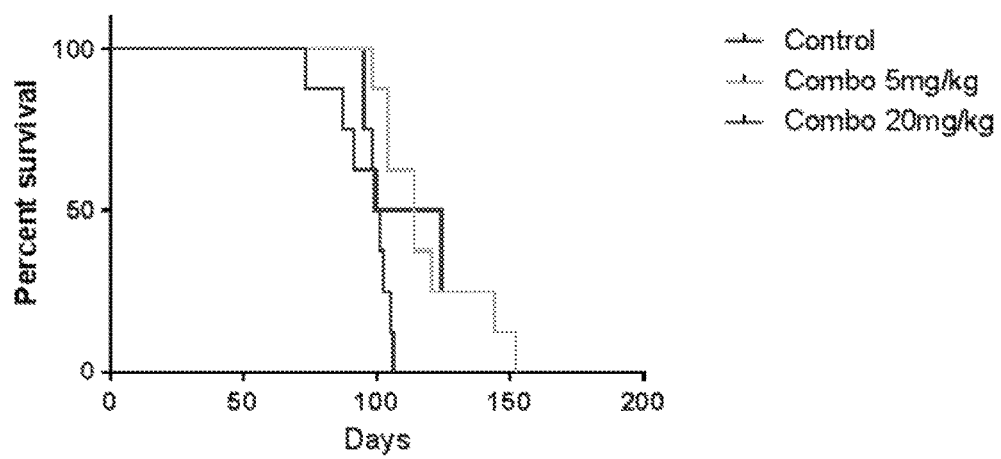
FIG. 2 is a graphical illustration comparing the percent survival of the mice treatment combination groups (ibudilast and temozolomide) and the control group post-treatment.

Significant survival advantages were observed for both combination groups (ibudilast 5 mg g TMZ and ibudilast 20 mg/kg and TMZ) (see FIG. 2).

These results demonstrate that ibudilast has a positive effect in the mouse glioblastoma model and that the ibudilast effect is dose dependent (20 mg/kg was more effective than 5 mg/kg), indicating that ibudilast may be effective for treating glioblastoma or recurrent glioblastoma. Additionally, the ibudilast effect was more evident for the combination of ibudilast and TMZ, indicating that ibudilast and TMZ in combination may be effective for treating glioblastoma or recurrent glioblastoma.

Example 2

Ibudilast and Temozolomide Efficacy in Balb/c Nude Mice Harboring Patient Derived Glioblastoma The same protocol is used as in Example 1 except the HW1 cell line is used instead of the RN1 cell line. The HW1 cell line is MGMT methylated and is susceptible to much lower levels of TMZ.

Similar results are shown as seen in Example 1, confirming that ibudilast and TMZ in combination may be effective for treating glioblastoma or recurrent glioblastoma.

Example 3

Human Studies

This is a single-center, open-label study to evaluate safety, tolerability and efficacy of ibudilast with recurrent grade 4 glioblastoma as adjunctive therapy. The duration of this study is one year. Ibudilast up to 100 mg/day is orally administered twice a day over 52 weeks in human subjects with confirmed grade 4 recurrent glioblastoma per brain MRI. Up to five patients are enrolled. Eligible subjects will consist of males and females age 18 or above. The study consists of a Screening Phase followed by a Treatment Phase (52 weeks), and a Follow-up Visit (within 4 weeks after the last dose).

Efficacy Points

The primary efficacy point is to evaluate the safety and tolerability of ibudilast as an adjunctive therapy for recurrent glioblastoma. The secondary efficacy point is to obtain pilot data on the efficacy of ibudilast as an adjunctive therapy of recurrent glioblastoma. MRI (Magnetic Resonance Imaging) is used to measure changes in brain tumor size ($cm^{2-}$). Survival time is assessed in addition to the time to cerebral edema requiring steroid rescue treatment.

Safety Endpoints

The proportion of subjects with:
Treatment-emergent adverse events (TEAEs)
Treatment-emergent serious adverse events (TESAEs)
Treatment discontinuations due to treatment-emergent adverse events Additional Safety Endpoints Laboratory measures (chemistry, hematology, urinalysis), vital signs, and 12 lead-electrocardiograms (ECGs).

Screening Phase

During the Screening Phase, subjects are assessed for study eligibility. The following assessments are performed: medical history including review of prior medications, physical examination including height and body weight, vital signs and an electrocardiogram. Other assessments include clinical labs, chemistry (including liver enzymes, gamma-glutamyl transferase, etc.), hematology, urinalysis and a serum pregnancy test.

Inclusion Criteria
1. Age 18 or above
2. Ability and willingness to signed informed consent form
3. Grade 4 GBM (glioblastoma multiforme), GBM, histologically confirmed, World Health Organization (WHO) criteria
4. Confirmed overexpression of macrophage inhibitory factor (MIF)/CD74 in GBM cell
5. Documented recurrence or progression after surgical resection/debulking, radiation and temozolomide chemotherapy.
6. Measurable contrast-enhancing progressive or recurrent GBM by MRI imaging before screening Exclusion Criteria
1. Acute intracranial or intra-tumoral hemorrhage>Grade 1 either by MRI or CT scan ≤2 weeks of screening (subjects with resolving hemorrhage changes, punctate hemorrhage or hemosiderin may enter the study)
2. Any significant laboratory abnormality which may put the subject at risk and with the following laboratory abnormalities at screening:
   Creatinine>1.7 mg/dL
   WBCs<3,000 mm$^3$
   Lymphocytes<800 mm$^3$
   Platelets<90,000 mm$^3$
3. Anticoagulation treatment with ≤1 mg/day coumadin ≤7 days prior to screening (low-dose [≤1 mg/day] coumadin, heparin, and low-molecular-weight heparin are permitted
4. Any systemic illness or unstable medical condition that night pose additional risk, including: cardiac, unstable metabolic or endocrine disturbances, renal or liver disease, past history of renal calculi, hyperinicemia, hypercalcemia, mitochondrial disease, known disorder of fatty acid metabolism, porphyria, carnitine deficiency and pancreatitis
5. History of non-glioma malignancy other than:
   Surgically excised non-melanoma skin cancer or in situ carcinoma of the cervix.
   A malignancy diagnosed ≥2 years ago if the subject has had no evidence of disease for 2 years prior to screening.
6. Active drug or alcohol dependence or any other factors that, in the opinion of the site investigators would interfere with adherence to study requirements
7. History of human immunodeficiency virus, or hepatitis C
8. Failure to recover from <Common Terminology Criteria for Adverse Events (CTCAE) grade 2 toxicities related to prior therapy
9. Pregnancy or breastfeeding
10. Use of any investigational drug within 1 month of enrollment Treatment Phase (52 Weeks)

Subjects who complete all of the screening assessments and meet all inclusion/exclusion criteria return to the clinic on. Treatment Day 1 to receive their first dose. Subjects are started on MN-166 30 mg BID. The dosage for the first two weeks is 30 mg BID and is subsequently titrated up to 50 mg BID, if tolerated. Afterwards, subjects return to the clinic on a regular basis (see FIG. 2, Schedule of Assessments) for 52 weeks. During the Treatment Phase, safety and efficacy parameters are assessed and concomitant medications are documented.

Individual Stopping Criteria

Subjects who experience an adverse event of Grade 2 nausea and/or diarrhea for greater than three consecutive days or Grade 3 nausea and/or vomiting for greater than one day thought to be related to ibudilast are discontinued from the study. Additionally, subjects who experience an adverse event of Grade 3 abdominal pain lasting for greater than one day thought to be related to ibudilast are discontinued from the study.

Study Stopping Rules

The study is stopped if two subjects experience a Grade 4 adverse event thought to be related to ibudilast.

Follow-Up Phase

All subjects who complete the study return for a follow-up visit (within 4 weeks from last dose) to assess adverse event status and to document concomitant medications.

Para. A. A method of treating a patient diagnosed with glioblastoma or suffering from recurrent glioblastoma comprising administering to the patient a therapeutically effective amount of ibudilast or a pharmaceutically acceptable salt thereof.

Para. B. The method of Para. A in which the ibudilast or pharmaceutically acceptable salt thereof is administered for at least 3 months.

Para. C. The method of Para. A in which the ibudilast or pharmaceutically acceptable salt thereof is administered for at least six months.

Para. D. The method of Para. A in which the ibudilast or pharmaceutically acceptable salt thereof is administered for at least one year.

Para. E. The method of Para. A in which the ibudilast or pharmaceutically acceptable salt thereof is administered for at least two years.

Para. F. The method of any one of Paras. A-F in which the ibudilast or pharmaceutically acceptable salt thereof is administered at least once daily.

Para. G. The method of any one of Paras. A-F in which the ibudilast or pharmaceutically acceptable salt thereof is administered orally.

Para. H. The method of any one of Paras. A-G in which the therapeutically effective amount of ibudilast or a pharmaceutically acceptable salt thereof is at least 30 mg/day.

Para. I. The method of any one of Paras. A-G, wherein the therapeutically effective amount of ibudilast or a pharmaceutically acceptable salt thereof is from 0.1 mg to 720 mg per day.

Para. J. The method of any one of Paras. A-H, wherein the therapeutically effective amount of ibudilast or a pharmaceutically acceptable salt thereof is from 30 mg to 200 mg per day Para. K. The method of any one of Paras. A-H, in which the therapeutically effective amount of ibudilast or a pharmaceutically acceptable salt thereof is 30 mg to 720 mg daily.

Para. L. The method of any one of Paras. A-G, in which the therapeutically effective amount of ibudilast or a pharmaceutically acceptable salt thereof is 60 mg to 600 mg daily.

Para. M. The method of any one of Paras. A-G, in which the therapeutically effective amount of ibudilast or a pharmaceutically acceptable salt thereof is 100 mg to 480 mg daily.

Para. N. The method of any one of Paras. A-G, in which the therapeutically effective amount of ibudilast or a pharmaceutically acceptable salt thereof is selected from the group consisting of 30 mg/day 60 mg/day, 90 mg day, 120 mg/day. 150 mg/day, 180 mg/day, 210 mg day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

Para. O. The method of any one of Paras. A-N, wherein the therapeutically effective amount is administered as a single dose or is divided into two, three, or four doses.

Para. P. The method of any one of Paras. A-O, wherein the ibudilast or a pharmaceutically acceptable salt thereof is administered as part of a combination therapy comprising at least one additional therapy.

Para. Q. The method of Para. P, wherein the at least one additional therapy comprises one or more of radiation therapy, one or more other therapeutic agent, or electric field therapy.

Para. R. The method of Para. Q, wherein the one or more other therapeutic agent is approved and known to have a utility in cancer.

Para. S. The method of Para. R, wherein the one or more other therapeutic agent is temozolomide, carmustine, bevacizumab, procarbazine, hydroxyurea, irinotecan, lomustine, nimotuzumab, sirolimus, mipsagargin, cabozantinib, lomustine, onartuzumab, patupilone (Epothilone B), recombinant oncolytic poliovirus (PVS-RIPO), or ally combination of one or more of the foregoing.

Para. T. The method of Para. R or Para. S, wherein the one or more other therapeutic agent is temozolomide.

Para. U. The method of Para. P, wherein the at least one additional therapy comprises laquinimod.

Para. V. The method of Para. P, wherein the ibudilast or a pharmaceutically acceptable salt thereof and the at least one additional therapy are both administered continuously.

Para. W. The method of Para. P, wherein the ibudilast or a pharmaceutically acceptable salt thereof is administered continuously and the at least one additional therapy is administered periodically.

Para. X. A method of treating a patient suffering from recurrent glioblastoma comprising administering to the patient a therapeutically effective amount of ibudilast or a pharmaceutically acceptable salt thereof.

Para. Y. The method of Para. X in which the ibudilast or pharmaceutically acceptable salt thereof is administered for at least 3 months.

Para. Z. The method of Para. X in which the budilast or pharmaceutically acceptable salt thereof is administered for at least six months.

Para. AA. The method of Para. X in which the ibudilast or pharmaceutically acceptable salt thereof is administered for at least one year.

Para. AB. The method of Para. X in which the ibudilast or pharmaceutically acceptable salt thereof is administered for at least two years.

Para. AC. The method of any one of Paras. X-AB in which the ibudilast or pharmaceutically acceptable salt thereof is administered at least once daily.

Para. AD. The method of any one of Paras. X-AC in which the ibudilast or pharmaceutically acceptable salt thereof is administered orally.

Para. AE. The method of any one of Paras. X-AD in which the therapeutically effective amount of ibudilast or a pharmaceutically acceptable salt thereof is at least 30 mg/day.

Para. AF. The method of any one of Paras. X-AD, wherein the therapeutically effective amount of ibudilast or a pharmaceutically acceptable salt thereof is from 0.1 mg to 720 mg per day.

Para. AG. The method of any one of Paras. X-AE, wherein the therapeutically effective amount of ibudilast or a pharmaceutically acceptable salt thereof is from 30 mg, to 200 mg per day Para. AH. The method of any one of Paras. X-AE, in which the therapeutically effective amount of ibudilast or a pharmaceutically acceptable salt thereof is 30 mg to 720 mg daily.

Para. AI. The method of any one of Paras. X-AD, in which the therapeutically effective amount of ibudilast or a pharmaceutically acceptable salt thereof is 60 mg to 600 mg daily.

Para. AJ. The method of any one of Paras. X-AD, in which the therapeutically effective amount of ibudilast or a pharmaceutically acceptable salt thereof is 100 mg to 480 rag daily.

Para. AK. The method of any one of Paras. X-AD, in which the therapeutically effective amount of ibudilast or a pharmaceutically acceptable salt thereof is selected from the group consisting of 30 mg/day, 60 mg/day, 90 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

Para. AL. The method of any one of Paras. X-AK, wherein the therapeutically effective amount is administered as a single dose or is divided into two, three, or four doses.

Para. AM. The method of any one of Paras. X-AL, wherein the ibudilast or a pharmaceutically acceptable salt thereof is administered as part of a combination therapy comprising at least one additional therapy.

Para. AN. The method of Para. AM, wherein the at least one additional therapy comprises one or more of radiation therapy, one or more other therapeutic agent, or electric field therapy.

Para. AO. The method of Para. AN, wherein the one or more other therapeutic agent is approved and known to have a utility in cancer.

Para. AP. The method of Para. AN or Para. AO, wherein the one or more other therapeutic agent is temozolomide, carmustine, bevacizumab, procarbazine, hydroxyurea, irinotecan, lomustine, nimotuzumab, sirolimus, mipsagargin, cabozantinib, lomustine, onartuzumab, patupilone (Epothilone B), recombinant oncolytic poliovirus (PVS-RIP0), or any combination of one or more of the foregoing.

Para. AQ. The method of Para. AO or Para. AP, wherein the one or more other therapeutic agent is temozolomide.

Para. AR. The method of Para. AM wherein the at least one additional therapy comprises laquinimod.

Para. AS. The method of Para. AM, wherein the ibudilast or a pharmaceutically acceptable salt thereof and the at least one additional therapy are both administered continuously.

Para. AT. The method of Para. AM, wherein the ibudilast or a pharmaceutically acceptable salt thereof is administered continuously and the at least one additional therapy is administered periodically.

Equivalents

It should be understood that although the present disclosure has been specifically disclosed by certain embodiments and optional features, modification, improvement and variation of the disclosures embodied disclosed herein may be resorted to by those skilled in the art, and that such modifications, improvements and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Marknsh groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

What is claimed is:

1. A method of treating a patient diagnosed with glioblastoma or suffering from recurrent glioblastoma comprising administering to the patient a therapeutically effective amount of ibudilast or a pharmaceutically acceptable salt thereof, as part of a combination therapy comprising at least one additional therapy, wherein the at least one additional therapy comprises laquinimod.

2. The method of claim 1 in which the ibudilast or pharmaceutically acceptable salt thereof is administered for at least 3 months.

3. The method of claim 1 in which the ibudilast or pharmaceutically acceptable salt thereof is administered at least once daily.

4. The method of claim 1 in which the ibudilast or pharmaceutically acceptable salt thereof is administered orally.

5. The method of claim 1, wherein the therapeutically effective amount of ibudilast or a pharmaceutically acceptable salt thereof is from 0.1 mg to 720 mg per day.

6. The method of claim 1, wherein the therapeutically effective amount is administered as a single dose or is divided into two, three, or four doses.

7. The method of claim 1, wherein the at least one additional therapy further comprises one or more of radiation therapy, one or more other therapeutic agent, or electric field therapy.

8. The method of claim 7, wherein the one or more other therapeutic agent is temozolomide, carmustine, bevacizumab, procarbazine, hydroxyurea, irinotecan, lomustine, nimotuzumab, sirolimus, mipsagargin, cabozantinib, lomustine, onartuzumab, patupilone (Epothilone B), recombinant oncolytic poliovirus (PVS-RIPO), or any combination of one or more of the foregoing.

9. A method of treating a patient suffering from recurrent glioblastoma comprising administering to the patient a therapeutically effective amount of ibudilast or a pharmaceutically acceptable salt thereof, as part of a combination therapy comprising at least one additional therapy, wherein the at least one additional therapy comprises laquinimod.

10. The method of claim 9 in which the ibudilast or pharmaceutically acceptable salt thereof is administered for at least 3 months.

11. The method of claim 9 in which the ibudilast or pharmaceutically acceptable salt thereof is administered at least once daily.

12. The method of claim 9 in which the ibudilast or pharmaceutically acceptable salt thereof is administered orally.

13. The method of claim 9, wherein the therapeutically effective amount of ibudilast or a pharmaceutically acceptable salt thereof is from 0.1 mg to 720 mg per day.

14. The method of claim 9, wherein the therapeutically effective amount is administered as a single dose or is divided into two, three, or four doses.

15. The method of claim 9, wherein the at least one additional therapy further comprises one or more of radiation therapy, one or more other therapeutic agent, or electric field therapy.

16. The method of claim 15, wherein the one or more other therapeutic agent is temozolomide, carmustine, bevacizumab, procarbazine, hydroxyurea, irinotecan, lomustine, nimotuzumab, sirolimus, mipsagargin, cabozantinib, lomustine, onartuzumab, patupilone (Epothilone B), recombinant oncolytic poliovirus (PVS-RIPO), or any combination of one or more of the foregoing.

* * * * *